(12) United States Patent
Keyes et al.

(10) Patent No.: US 10,012,554 B2
(45) Date of Patent: Jul. 3, 2018

(54) BALLISTIC IMPACT DETECTION SYSTEM (71) Applicants: Carolyn Keyes, Concord, NH (US); Nicholas Potvin, Merrimack, NH (US); Zachary Richards, Londonderry, NH (US); Christopher Tolisano, Somers, CT (US)

(72) Inventors: Carolyn Keyes, Concord, NH (US); Nicholas Potvin, Merrimack, NH (US); Zachary Richards, Londonderry, NH (US); Christopher Tolisano, Somers, CT (US)

(*) Notice: Subject to any disclaimer, the term of this patent is extended or adjusted under 35 U.S.C. 154(b) by 0 days.

(21) Appl. No.: 15/454,635

(22) Filed: Mar. 9, 2017

(65) Prior Publication Data

US 2017/0261386 A1    Sep. 14, 2017

Related U.S. Application Data (60) Provisional application No. 62/306,295, filed on Mar. 10, 2016.

(51) Int. Cl.
| | |
|---|---|
| *G08B 21/00* | (2006.01) |
| *G01L 1/22* | (2006.01) |
| *G01L 1/16* | (2006.01) |
| *G06Q 50/26* | (2012.01) |
| *A61B 5/00* | (2006.01) |
| *A41D 1/04* | (2006.01) |
| *A41D 1/00* | (2018.01) |
| *G08C 19/04* | (2006.01) |
| *F41H 1/02* | (2006.01) |

(52) U.S. Cl.
CPC ............ *G01L 1/2256* (2013.01); *A41D 1/002* (2013.01); *A41D 1/04* (2013.01); *A61B 5/7465* (2013.01); *F41H 1/02* (2013.01); *G01L 1/16* (2013.01); *G06Q 50/265* (2013.01); *G08C 19/04* (2013.01)

(58) Field of Classification Search
CPC ............................ A42B 3/046; A61B 2503/10
USPC ............................................ 340/668, 539.11
See application file for complete search history.

(56) References Cited

U.S. PATENT DOCUMENTS

| | | | | |
|---|---|---|---|---|
| 4,659,090 | A | * | 4/1987 | Kustanovich ........... G01L 1/144 273/376 |
| 6,349,201 | B1 | | 2/2002 | Ford |
| 2010/0315226 | A1 | | 12/2010 | Chu |

(Continued)

*Primary Examiner* — Fabricio R Murillo Garcia
(74) *Attorney, Agent, or Firm* — Chapin IP Law, LLC (57) ABSTRACT A protective garment contains a projectile detection device, in addition to impact and breach resistant materials for protecting the wearer. An arrangement of force sensitive regions defines a grid arrangement responsive to an incoming projectile. The force sensitive regions include pressure sensitive or piezoelectric characteristics such that an impact varies the electrical response of each region. A detection circuit connects to each region for sampling. A sampling of the regions computes a high velocity impact by a sudden change in the sensed electrical characteristics, such as a sudden drop in resistance between two planer sheets. The grid arrangement identifies the impact placement on the garment, and can be mapped to anatomical regions to evaluate a severity. Placement and impact force, along with GPS coordinates of the wearer, are transmitted by the detection circuit and/or in conjunction with an app on a mobile device of the wearer for alerting first responders.

19 Claims, 9 Drawing Sheets

(56) References Cited

U.S. PATENT DOCUMENTS

| | | |
|---|---|---|
| 2011/0209259 A1 | 9/2011 | Chu |
| 2014/0144235 A1* | 5/2014 | Suzuki ................. G01P 15/125 |
| | | 73/514.32 |
| 2016/0018278 A1* | 1/2016 | Jeter, II ................ G01L 5/0052 |
| | | 340/665 |

* cited by examiner

BALLISTIC IMPACT DETECTION SYSTEM

RELATED APPLICATIONS

This patent application claims the benefit under 35 U.S.C. § 119(e) of U.S. Provisional Patent App. No. 62/306,295, filed Mar. 10, 2016, entitled "PROTECTIVE VEST," incorporated by reference in entirety.

BACKGROUND

Protective garments for first responders, law enforcement and others confronted with an unknown and potentially hazardous environment provide protection against projectiles such as gunfire, shrapnel and other hazardous objects. Colloquially known as "bulletproof vests," such garments may take the form of body armor or other encapsulating covering for ensuring the wearer's safety against harmful or hostile activity.

SUMMARY

A protective garment contains a projectile detection device, in addition to impact and breach resistant materials, for protecting the wearer. An arrangement of force or pressure sensitive regions defines a grid arrangement responsive to an incoming projectile. The force sensitive regions include pressure sensitive or piezoelectric characteristics such that an impact varies the electrical response of each region. A detection circuit connects to each region for sampling. A sampling of the regions computes a high velocity impact by a sudden change in the sensed electrical characteristics, such as a sudden drop in resistance between two planer sheets. The grid arrangement identifies the impact placement on the garment, and can be mapped to anatomical regions to evaluate a severity of possible wearer injury. Placement and impact force, along with GPS coordinates of the wearer, are transmitted by the detection circuit and/or in conjunction with an app on a mobile device of the wearer for alerting first responders.

In an example configuration, the projectile detection device includes opposed orthogonal strips of a selectively conductive, pressure sensitive or piezoelectric planar material adapted for electrical communication in response to a compressive force, such that the electrical communication defines a position of the compressive force based on corresponding locations on each of the opposed sheets of the selectively conductive material.

Configurations herein are based, in part, on the observation that conventional approaches to protective vests and body armor provide only impact protection. Unfortunately, conventional uses of so-called "bulletproof" vests suffer from the shortcoming that they may not accommodate a need for subsequent remedial care to complement the life-saving operation of the vest. Conventional approaches exhibit no evaluation of the location and severity of the impact for evaluating wearer condition and notifying first responders if the wearer is in need of further assistance. Such vests can still result in a blunt force injury due to dispersed impact energy, or may suffer from outright breach from merely slowing, rather than stopping, the projectile. Accordingly, configurations herein substantially overcome the above-described shortcomings by providing a protective garment having an array of impact sensors and a detection circuit for sampling and analyzing the sensors for identifying a force and location of the absorbed impact. An associated personal electronic device such as a smartphone is responsive to the detection circuit for transmitting, along with a GPS (Global Positioning System) position of the wearer, to a first responder or other monitoring entity so that appropriate remedial care may be initiated. The impact sensor is expected to take the form of a resistive, piezoelectric, or other electromechanical element for delivering a varied voltage or current in response to physical agitation. In an example arrangement, the projectile detection device defines a grid, and the generated voltage characteristics are indicative of a grid position of the sensed impact.

The grid arrangement may be implemented such that the impact detection device further includes a selectively resistive piezoelectric layer and at least one conductive layer, and the generated voltage characteristics define the grid position of the sensed impact by varied resistance of the conductive layer at the indicated grid position resulting from compression of the selectively resistive layer. In such a configuration, the impact detection layer further includes at least one piezoelectric layer disposed between opposed conductive layers, and the grid is defined by perpendicularly offset strips of the opposed conductive layers such that the piezoelectric layer is adapted to vary the voltage characteristics proportionally to the force of the sensed impact. In other words, the compression of the layers resulting from the impact vary the resistance at the selectively resistive layer for detection by the impact detection circuit.

A particular configuration includes implementations where the selectively resistive layer is Velostat™ and the conductive layer includes at least one of pure copper polyester taffeta fabric (PCPF) or Ripstop Silver Fabric (RSF). In a specific example discussed in detail below, the projectile detection device for a protective garment includes an electrically resistive mesh disposed between opposed planar sheets of a selectively conductive material, such that the opposed planar sheets are configured for electrical communication in response to pressure, and a plurality of conductive members for applying a voltage to each of the opposed planar sheets. A detection circuit identifies an electrical communication between the opposed planar sheets, such that the detection circuit is configured for determining, based on the identified electrical communication, a severity and location of a projectile impact causing a compressive force.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Configurations below depict a particular example of a protective garment having projectile impact sensors and coupled to a personal electronic device such as a smartphone for identifying a force and location of the absorbed impact, and transmitting, along with a GPS (Global Positioning System) position of the wearer to a first responder or other monitoring entity so that appropriate remedial care may be initiated.

Although the use of bullet-resistant vests has saved the lives of both law enforcement officers and military personnel, wearers are commonly left with injuries which can be life-threatening or fatal. The purpose of bullet-resistant vests, along with other types of body armor, is to prevent the penetration of a projectile by distributing the force that it exerts on the wearer across a wide area. However, conventional vests provide no support to the wearer after impact absorption. A wearer of a bullet-resistant vest may often require immediate medical attention even absent projectile penetration. However, first responders may not know that the wearer needs assistance, and may not know the wearer location, especially if the individual is incapacitated or otherwise unable to call for help.

Figure 1:
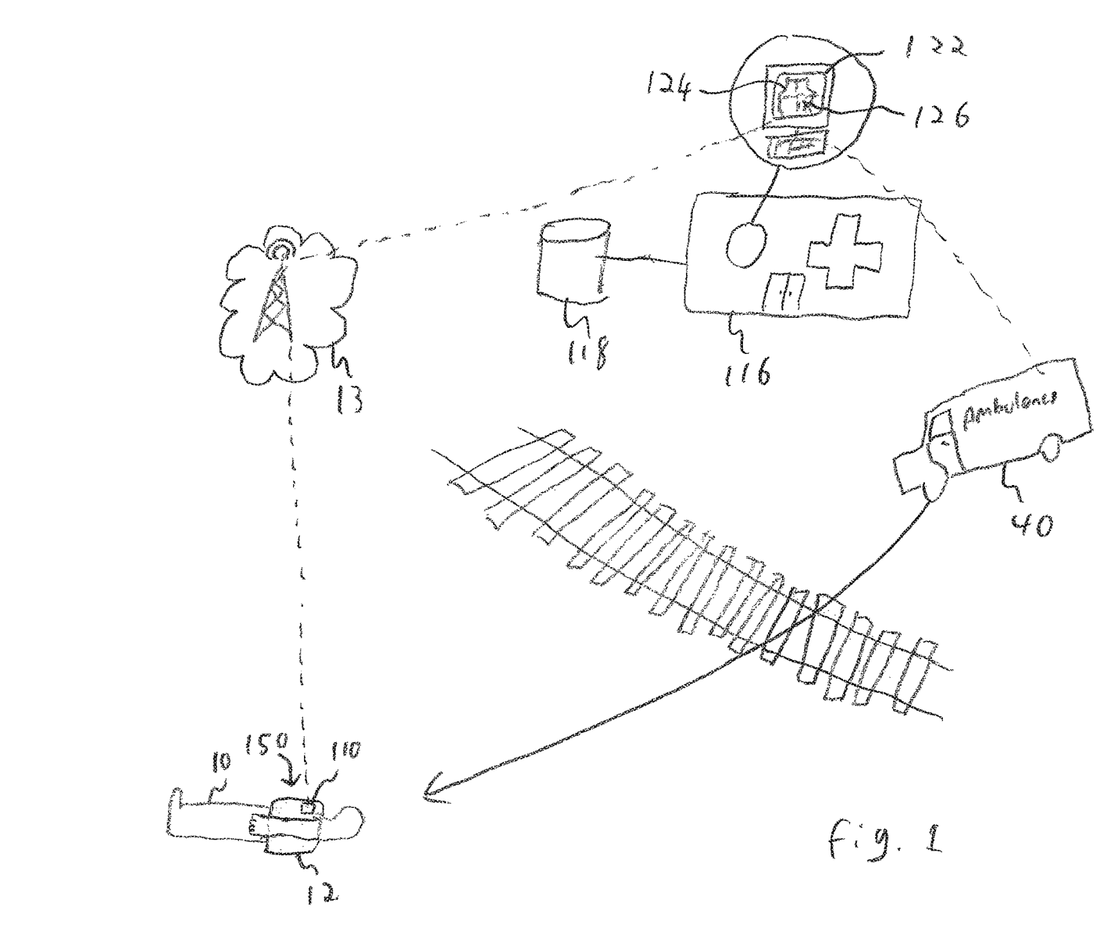
FIG. 1 is a context diagram of a first responder environment suitable for use with configurations herein.

FIG. 1 is a context diagram of a first responder environment suitable for use with configurations herein. Referring to FIG. 1, a vest wearer 10 wears a protective garment 12, such as a "bulletproof" vest or body armor, having a detection circuit 110. The detection circuit 110 is operable, alone or in conjunction with a personal electronic device, to transmit a projectile detection message 112 to a first responder dispatch 116 via a public access network 13 such as the Internet. A communications interface accessible via the detection circuit 110 is configured to transmit the projectile detection message 112 including an impact severity indicative of a projectile speed and force, and a location indicative of an injury site to the first responder dispatch 116. The first responder dispatch 116 receives the detection message 112 and renders, on a GUI 122, a placement image 124 indicative of an impact location 126 on the protective garment 12. In the example shown, the placement image 124 indicates an impact in the lower left abdomen region, which generally permits a greater time for a successful response than an upper chest location indicative of a possible heart injury. Appropriate decisions for dispatching first responders 40 may be made based on the exigency called for based on the placement image. A ballistics database 118, may store a signature based on information in the detection message 112 for comparison with other signatures to identify the projectile and type of weapon involved.

Conventional approaches, in contrast, do not indicate a location or severity, but rather only existence of an impact. U.S. Patent Pub. No. 2011/0209259 presents a GPS signal indicative of a vest impact, but has no teaching of an impact severity or impact location on the user. U.S. Pat. No. 6,349,201 suggests impact detection and a transmitted indication, but no clarifying information of location or impact severity.

The projectile detection device takes the form of a flexible planar assembly adapted for adherence or integration with a protective vest or other impact absorbing structure. An interface to a detection circuit 110 is provided by a wired or wireless (e.g. Bluetooth®) linkage, and may involve a mobile device for the projectile detection, impact analysis and projectile detection message 112 transmission.

Figure 2A:
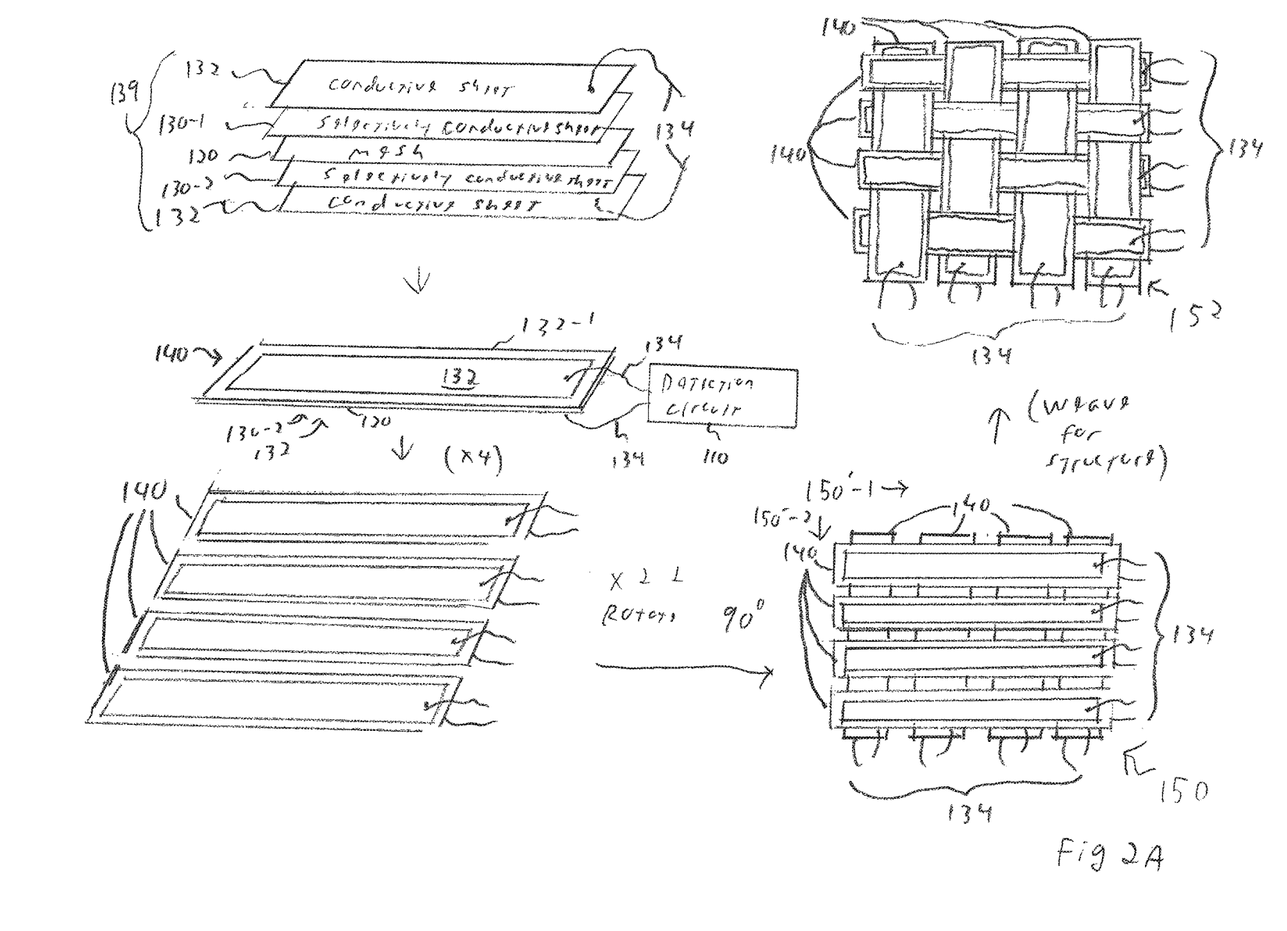
FIGS. 2A and 2B show an exploded view of the projectile detection device in the environment of FIG. 1.
Figure 2B:
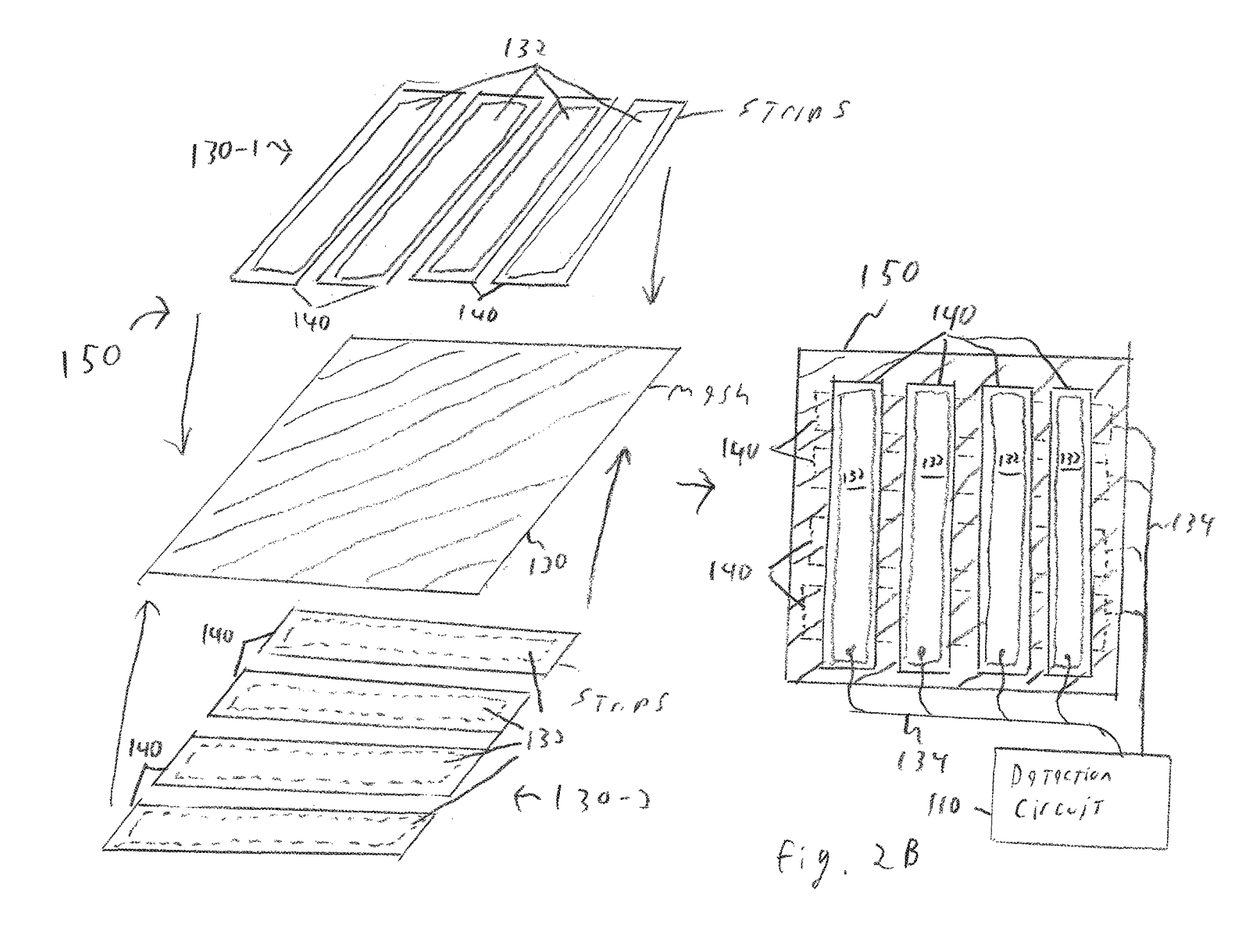

FIGS. 2A and 2B show exploded views of particular configurations of the projectile detection device in the environment of FIG. 1. Referring to FIGS. 1 and 2A, an electrically resistive mesh 120 is disposed between opposed planar sheets 130-1, 130-2 (130 generally) of a selectively conductive material, in which the opposed planar sheets 130 are configured for electrical communication in response to pressure. A plurality of conductive members 132 connect to the detection circuit 110 for applying a voltage to each of the opposed planar sheets 130. The selectively conductive material may be a material with piezoelectric or pressure-sensitive resistive (PSR) properties such as Velostat™ and the conductive members 132 are a substantially conductive material such as Copper Polyester Taffeta Fabric (PCPF) or Ripstop Silver Fabric (RSF). Other suitable materials having the disclosed electric properties will also suffice. The layers 120, 130 and 132 are bonded or secured together to form a layered assembly 139 or "sandwich" defining a single pressure impact sensor.

Since the conductive member 132 extends across the entire sensing area, configurations herein are operable with a single continuous layered assembly for detecting impact. However, a location of the impact may be localized by subdividing the layered assembly 139 into a series of strips 140, each covering a particular region or area of the vest 12.

An application of pressure or force to the selectively conductive material compresses the planar sheet 130 layer and the mesh 120 to sufficient degree to cause an electrical communication through the mesh 120 with the conductive material sheet 130 layer on the other side of the mesh 120. A combination of mesh compression and pressure induced conductivity (inverse resistance) in the sheet 130 causes an inductive or conductive electric communication across the mesh 120 and to the conductive members 132 on the opposed side.

The conductive members 132 further comprise a conductive sheet disposed on the selectively conductive material, in which the conductive members 132 connect to the detection circuit via wires 134 or other suitable communication. The opposed conductive sheets 130 are therefore defined by opposed orthogonal strips 140 of the selectively conductive planar material adapted for electrical communication in response to a compressive force. Such electrical communication defines a position of the compressive force based on corresponding locations on each of the opposed sheets 132 of the selectively conductive material. The selectively conductive material sheet 130, as shown in FIG. 2A, is subdivided into a plurality of strips 140, and arranged orthogonally and/or woven with a second set of strips 140. The orthogonal strips 140 form an impact detection assembly 150 defining a layered grid. The strips 140 need not be arranged orthogonally in a grid, but rather could take any suitable layered arrangement such that an impact to a common location of two or more strips 140 yields an impact reading, and a correlation of strips 140 bearing an impact reading therefore designating the location at the overlapping or intersecting region of the impacted strips. It should also be understood that any suitable arrangement of strips would involve wrapping, insulating, or otherwise packaging the strips 140 so as to not contact and cause shorts between the conductive members 132 of adjacent strips 140.

As indicated above, a projectile impact on the selectively conductive sheet 130-1 of any size will result in a detectable voltage and/or current across the mesh to the opposed sheet 130-2. In the configuration of FIG. 2A, the opposed planar sheets therefore 130 further comprise a series 150'-1 of elongated strips 140 longitudinally adjacent and parallel to other strips 140 of the series, and orthogonal to a second series 150'-2 of strips 140 opposed or interwoven with the first series 150'-1. The interwoven grid 152 secures the strips into a single, flexible unit adapted for installation onto the vest 12.

Since the orthogonal strips 140 on each side of the mesh 120 run parallel to the strips on the same series 150' and orthogonal to the strips on the opposed series 150', the strips 140 define a grid having intersecting regions based on strips overlapping at a common position. When a connection is made across the mesh 120, a variably resistive connection is established from between opposed planar sheets 130-1 to 130-2.2. Due to the overlapping grid structure 150, the impact will affect two intersecting strips on the grid. Since the strips run orthogonal or perpendicular to the opposed side, the intersection of the strips 140 gives the location of the impact.

FIG. 2B shows an alternate construction with the strips integrated to contact with the opposed perpendicular strips. In the configuration of FIG. 2B, the protective vest 12 includes a electrically resistive mesh 120 disposed between opposed planar sheets 130-1, 130-2 (130 generally) of a selectively conductive material, in which the opposed planar sheets 130 are configured for electrical communication in response to pressure across the common mesh 120. The strips 140 are integrated across a mesh common to both series 150' of strips. Electrical communication between the strips 140 occurs by a connection to an opposed strip 140 of the orthogonal series 150'.

Figure 3:
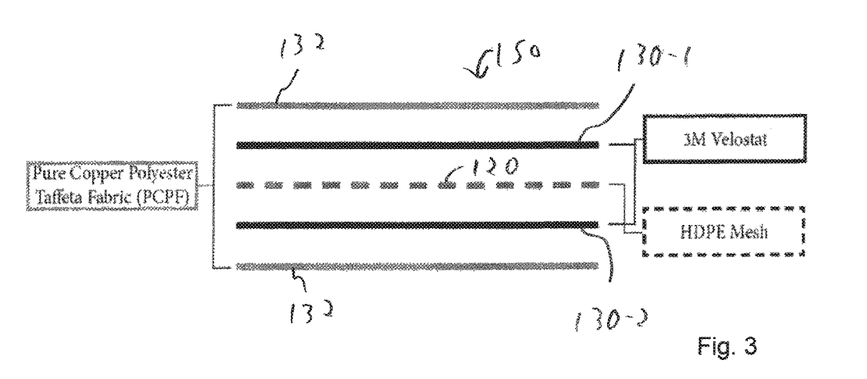
FIG. 3 shows a cross section of the layers in the projectile detection device of FIG. 2.

FIG. 3 shows a cross section of the strip layers in the projectile detection device of FIG. 2. Referring to FIGS. 2 and 3, the impact detection assembly 150 is a flexible, layered structure. The outermost layer is a flexible conductive fabric for defining the conductive members 132 to provide a substantially equal electric field or charge across the area defined by the strips 140. The conductive sheet generally comprises a continuous conductive material having a low resistance sufficient to maintain a similar voltage across the conductive sheet. In the example arrangement, this may be fulfilled by PCPF, RSF or another suitable conductive material such as foils or textile based conductive approaches.

The selectively resistive material defines the opposed planar sheets 132, and has piezoelectric properties for exhibiting a variance in electrical characteristics in response to pressure. The material generally has a lower resistance in response to compressive force of an impact, up to a maximum electrical flow similar to a closed circuit connection. When formed into the strips 140, the selectively conductive layer is cut slightly larger than the conductive members 132 to avoid shorting between opposed members 132. A limiting resistor may be employed to regulate current flow from a "railed" sensor. Velostat™ or another pressure sensitive variably resistive material may be employed. The middle mesh layer 120 separates the opposed planar sheets 132 and limits electrical communication until a pressure response based on impact is induced. Thus, the mesh 120 is an insulative material having a high resistance and is adapted to permit electrical conduction or induction between the opposed planar sheets 132 in response to compression or pressure as in a projectile impact.

The opposed strips 140 and the mesh 120 therefore form the layered structure responsive to a projectile impact such that electrical communication between the strips 140 on opposed sides indicates a lowest resistance at a location of greatest compressive force from the projectile. The detection circuit 110 determines, based on a point of maximum conduction between the opposed planer sheets 130, an impact location. The grid arrangement, now discussed in FIG. 4 below, identifies this point of lowest resistance to identify placement of the projectile corresponding to an injury location on the wearer 10.

Figure 4:
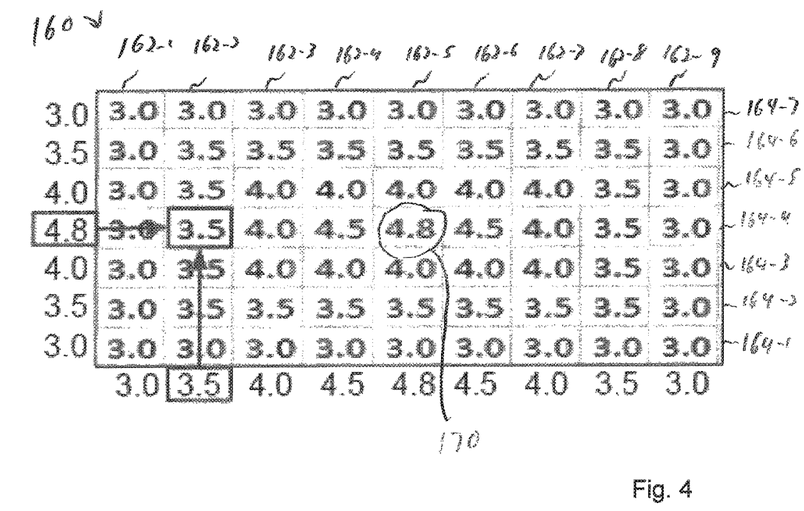
FIG. 4 shows a grid defined by the strips in the layers of FIG. 3.

FIG. 4 shows a grid 160 defined by the strips in the layers of FIG. 3. The layered structure of the impact detection assembly 150 implements the grid of FIG. 4. The opposed strips 140 each define rows and columns of the grid 160. The strips 140 on one side of opposed planer sheets 130-1 define columns 162-1 . . . 162-9 (162 generally), and the strips 140 defining the opposed planar sheets 132-2 define rows 164-1 . . . 164-7 (164 generally). It should be apparent that any suitable number of rows 164 and columns 162 may be implemented depending on the granularity of detection. Even a 2*2 arrangement provides valuable information as to the quadrant of a torso.

In operation, the conductive layer 132 defines an electrode coupled between each strip 140 and the detection circuit 110, such that the detection circuit 110 is configured to identify a location on the grid 160 based on an intersection of strips 140 having the lowest resistance on each of the opposed sides 130 of the mesh. Since each strip extends transverse to all the opposed strips 140 on the other side, a sampled electric reading for each electrode (row 164 or column 162) will yield the greatest conductivity of any row/column intersection of that strip. As shown in the example, the intersection of column 162-2 and row 164-4 is read as a row value of 4.8 v because that is the highest voltage reading in the row 164-4. Similarly, column 162-2 reads 3.5 v as the highest in that column.

To find the impact, the greatest electrical communication between the opposed sides 130 indicates the greatest pressure or impact force. Circled plot 170, corresponding to column 162-5, row 164-4 shows the point of impact, being the intersection of the highest row and column values of 4.8 v. Note that the example arrangement employs a voltage value as the indicator of electrical communication. Alternate approaches may employ current detection or other electrical sensing mediums for grid interpretation.

The detection circuit 110 is configured to sample each of the strips 140 for an electrical communication with the strips 140 on the opposed side 130 and identify an impact when the electrical communication attains a threshold indicative of a projectile impact. The electrodes or wires 134 to the opposed strips 140 having the lowest resistance, and thus greatest voltage, are indicative of the grid 160 position at which the impact occurred, in which the grid 160 corresponds to injury locations on the wearer 10 of the protective garment.

In the example configuration, sensing proceeds as follows. A voltage will be applied to the top layer of conductive fabric and the layers of Velostat act to resist the flow of electrical current from the top and bottom pieces of conductive fabric. As pressure is applied to the sensor strip 140, the three sections are compressed together and the resistivity of the Velostat is reduced. The voltage difference between the two sections of conductive fabric is reduced and can be measured by the system. The sensor strips (acting as a resistor) may be paired with a fixed resistor to form a voltage divider and allow calibration or fine-tuning to suit construction of different materials. A measurement is taken the voltage across the fixed resistor. The voltage across the fixed resistor can be calculated as follows:

$$V_f = V_s * \left\lfloor \frac{R_f}{R_f + R_s} \right\rfloor$$

where $V_s$ is the voltage provided by the voltage source, $R_f$ being the fixed resistor and $R_s$ variable resistor, namely the sensor strip. The value of the fixed resistor will be chosen to be close to that of the resting resistance of the sensor strip, giving the sensor the most clarity.

Figure 5:
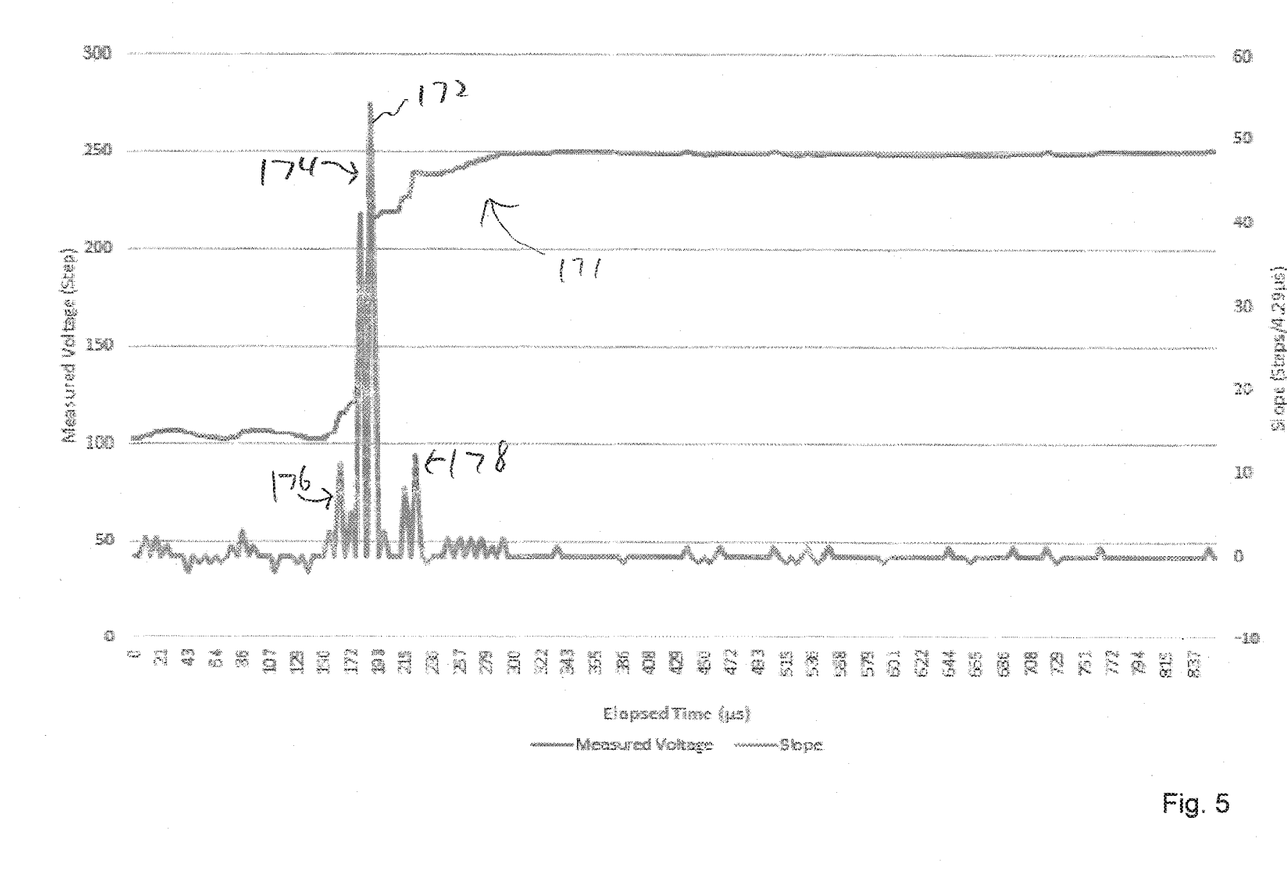
FIG. 5 shows a sampling graph of sampled readings from the grid of FIG. 4.

FIG. 5 shows a sampling graph of sampled readings from the grid of FIG. 4. Referring to FIGS. 4 and 5, the detection circuit 110 is configured to sample a series of measurements indicative of the electrical communication and compute a change in the compressive force over time, such that a predetermined increase in the compressive force is indicative of the projectile impact. In other words, over a series of sampled readings, a computed slope indicates the impact severity. The detection circuit 110 is configured to compute an impact slope based on a sampling frequency and a decrease in resistance between samplings, such that the impact slope is indicative of a ballistics type of a projectile causing the projectile impact. Generally, sampling is performed on the grid location 170 exhibiting the greatest impact, however multiple grid locations could be analyzed given sufficient sampling capability.

In the example configuration, the output voltage values from the individual strips of the sensor grid will range from 0 to 3.3 Volts. The values of these strips will be rapidly changing during the impact of the bullet and therefore the system acquiring the changing data values must be sufficiently fast. Each changing analog signal from a strip must be converted to a digital signal before it can be processed. In order to reduce the number of components needed to build the system, a four channel analog to digital converter (ADC) was selected. Each input channel of the ADC will correspond to one sensor strip. The four input channels will be sampled sequentially for analysis. The selected chip is an ADC084S101 manufactured by Texas Instruments. This ADC can convert with 8-bit precision, yielding a possible range of 256 discrete Voltage readings (from 0 to 255). Analog voltage is converted to a digital value from a conversion:

$$S = \left\lfloor \frac{V}{3.3} * 255 \right\rfloor$$

This converter can sample at 1 MHz, which must be split across the input channels, resulting in each sensor strip being polled at 250 kHz. After the polling of all four strips and the completion of the conversion, the chip repeats the process. Testing with ballistic fire on a bullet-resistant vest confirmed that a sample rate of 250 kHz sufficiently maps the impact of the bullet. This sampling rate results in a sample being taken once every 4 μs (and one snapshot taken every 16 μs).

In order to operate, the ADC requires two clock signals, a 1 MHz chip select (CS) and a 16 MHz serial clock (SCLK). The CS instructs the ADC when to take a sample and the SCLK controls the output of the digital bitstream into the FPGA. The ADC receives inputs from the four sensor strips 140 that comprise the grid 160 as well as a 3.3 V power supply via the detection circuit 110. The chip also needs an input dictating which channel to sample in the next cycle, written as a binary number into the chip's control register. The ADC then outputs a bitstream of the digital voltage values to the FPGA for data processing. The ADC is mounted on a custom designed printed circuit board (PCB). The PCB allows for short connecting traces between the ADC and other components in the circuit, allowing operation at high frequencies.

As shown in FIG. 5, depicting the impact from grid location 170, a dominant peak 172 in the graph 171 indicates an impact. The slope 174 leading up to this peak 172 may be analyzed against a threshold to ascertain the impact, and also for computing a velocity or force for identifying the ballistic item (e.g. weapon or bullet) causing the impact. Adjacent peaks 176, 178 indicate a reverberation or impact induced wave, and may be employed in computing and comparing a ballistic signature for identifying weapons and projectiles, discussed further below in FIG. 8.

Figure 6A:
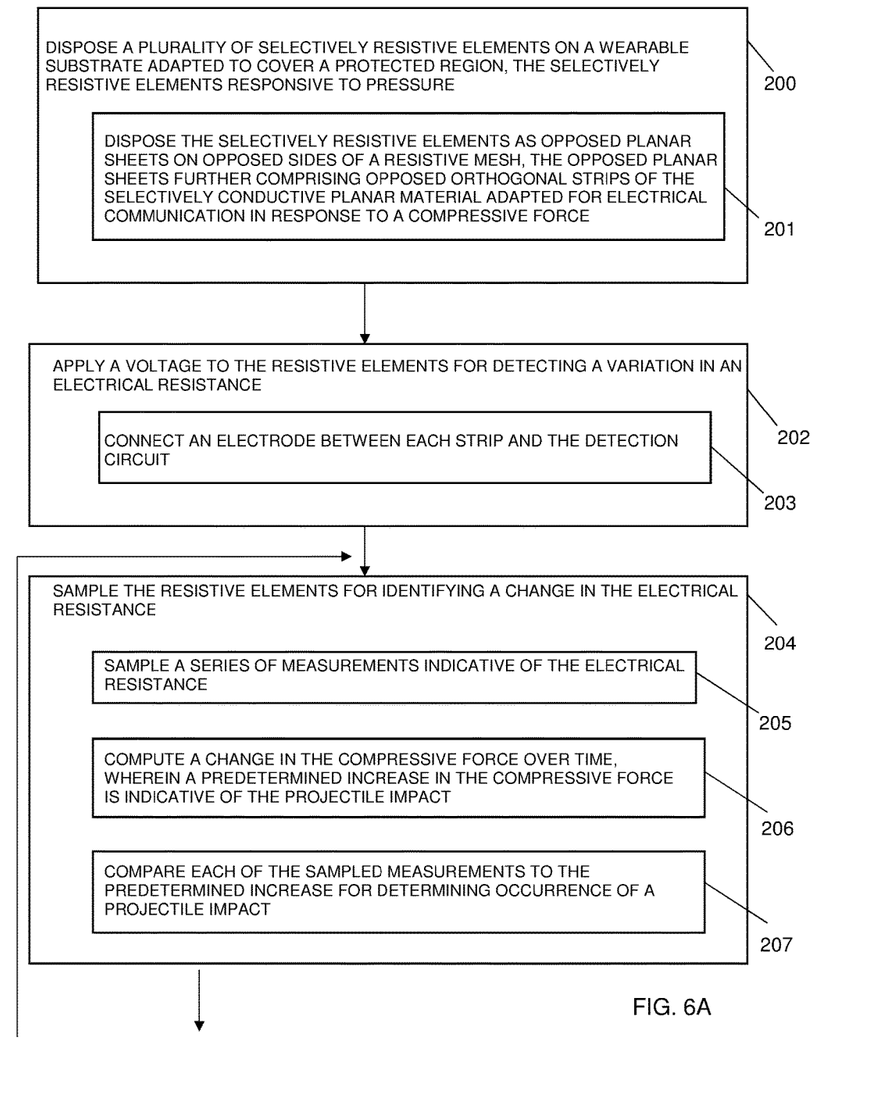
FIGS. 6A and 6B show a flowchart of projectile impact detection using the readings as in FIG. 5.
Figure 6B:
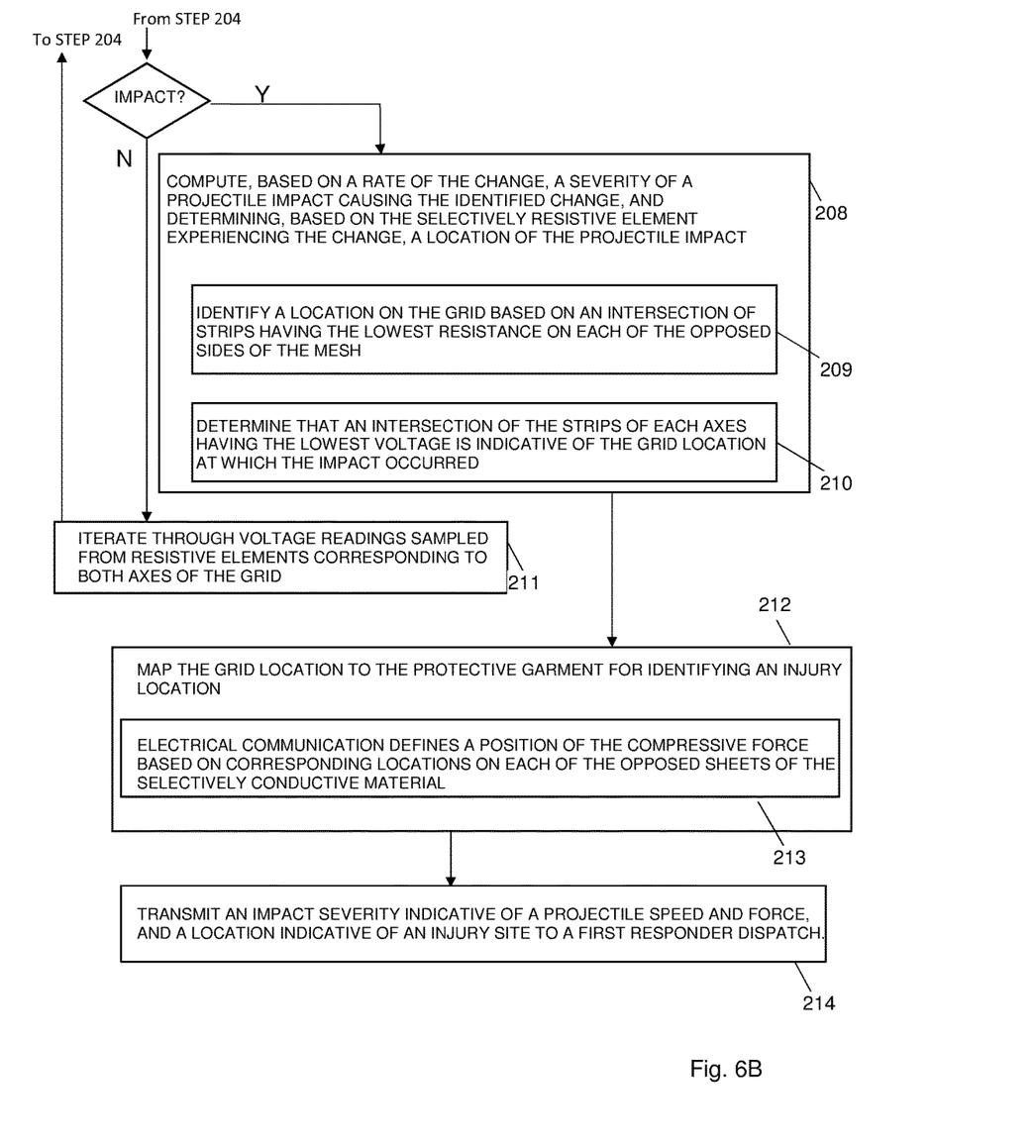

FIGS. 6A and 6B show a flowchart of projectile impact detection using the readings as in FIG. 5. Referring to FIGS. 2-6B, in a particular example, the method of detecting an impact and placement of a projectile as disclosed herein includes, at step 200, disposing a plurality of selectively resistive elements on a wearable substrate adapted to cover a protected region, such that the selectively resistive elements are responsive to pressure. This includes disposing the selectively resistive elements as opposed planar sheets 130 on opposed sides of a resistive mesh 120, such that the opposed planar sheets 130 further comprising opposed orthogonal strips 140 of the selectively conductive planar material adapted for electrical communication in response to a compressive force, as depicted at step 201.

The detection circuit 110 applies a voltage to the resistive elements for detecting a variation in an electrical resistance, as shown at step 202, by connecting an electrode or wire 134 between each strip 140 and the detection circuit 110, depicted at step 203. The detection circuit 110 samples the resistive elements for identifying a change in the electrical resistance, as shown at step 204, which includes sampling a series of measurements indicative of the electrical resistance (step 205), computing a change in the compressive force over time, wherein a predetermined increase in the compressive force is indicative of the projectile impact (step 206), and comparing each of the sampled measurements to the predetermined increase for determining occurrence of a projectile impact, at step 207. This corresponds to identifying the slope 174.

If a projectile impact is detected, the detection circuit 110 computes, based on a rate of the change of slope 174, a severity of a projectile impact causing the identified change, and determines, based on the selectively resistive element experiencing the change, a location of the projectile impact, as depicted at step 208. The detection circuit 110 identifies a location (e.g. 170) on the grid 160 based on an intersection of the strips 140 having the lowest resistance, and hence the greatest voltage, on each of the opposed sides 130 of the mesh 120, as shown at step 209. The detection circuit 110 determines that an intersection of the strips 140 of each axes (defined by rows 164 and columns 162) that has the lowest voltage is indicative of the grid 160 location at which the impact occurred, 170 in this case, depicted at step 210.

The detection circuit iterates through voltage readings sampled from resistive elements corresponding to both axes of the grid until a determination of an impact is made, as shown at step 211.

Following impact determination, the detection circuit maps the grid 160 location to the protective garment for identifying an injury location, as shown at step 212. This may correspond to the vest quadrant 126, or may be more granular depending on the rows 164 and columns 162 in the grid 160. In this step, the electrical communication defines a position on the grid 160 of the compressive force based on corresponding locations on each of the opposed sheets 130 of the selectively conductive material, as depicted at step 213.

The detection circuit, either alone or via a smartphone app, transmits an impact severity 112 indicative of a projectile speed and force, and a location indicative of an injury site to a first responder dispatch 116, as depicted at step 214.

Figure 7:
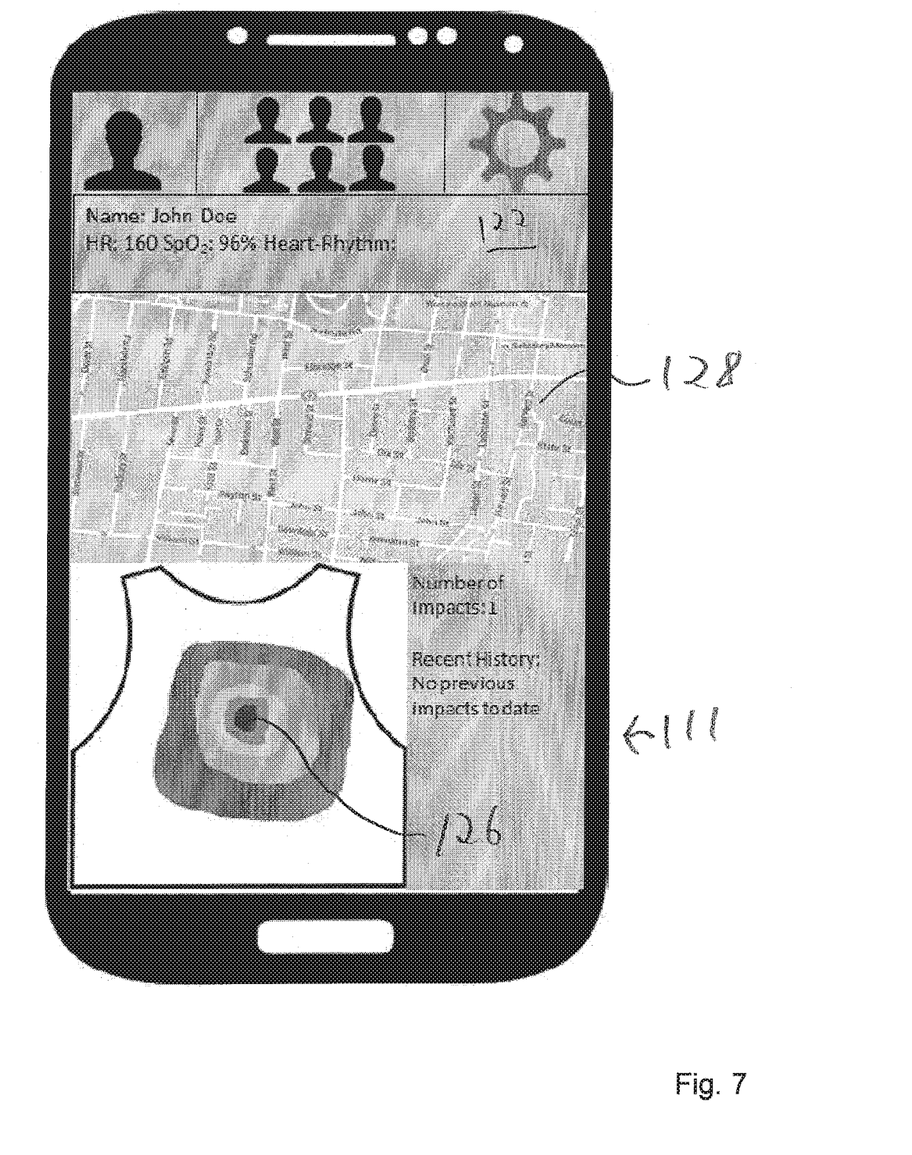
FIG. 7 shows a GUI interface on a device coupled to the detection circuit of FIGS. 2-5.

FIG. 7 shows a GUI interface on a device 111 coupled to the detection circuit of FIGS. 2-5. Referring to FIG. 7, transmission of the impact incident message 112 to a first responder facility 116 for assuring prompt follow up and remedial care is paramount. Accordingly, the interface further includes a transmission medium adapted for communication to a personal electronic device appurtenant to the wearer, such that the personal electronic device is operable to transmit a position of the wearer and the location 128 of the sensed impact to the responsive entity. In a particular arrangement, this would be the wearer's cellphone coupled via Bluetooth to the interface. Alternate arrangements may employ a Zigbee® link or mesh network and/or a local on-site responder, however any suitable wireless medium will suffice. It should be noted that a first transmission medium defines the communication from the interface to the personal electronic device, and a second transmission medium for transmission to the responsive entity, such that the first transmission medium is a short range medium and the second transmission medium is a long range medium. In an example configuration, the first transmission medium is Bluetooth and the second transmission medium is a cellular medium. In this manner, a geographic location and severity of a projectile penetration may be transmitted to a monitoring entity either in the first responder facility 116 and/or a suitable mobile device 111.

Figure 8:
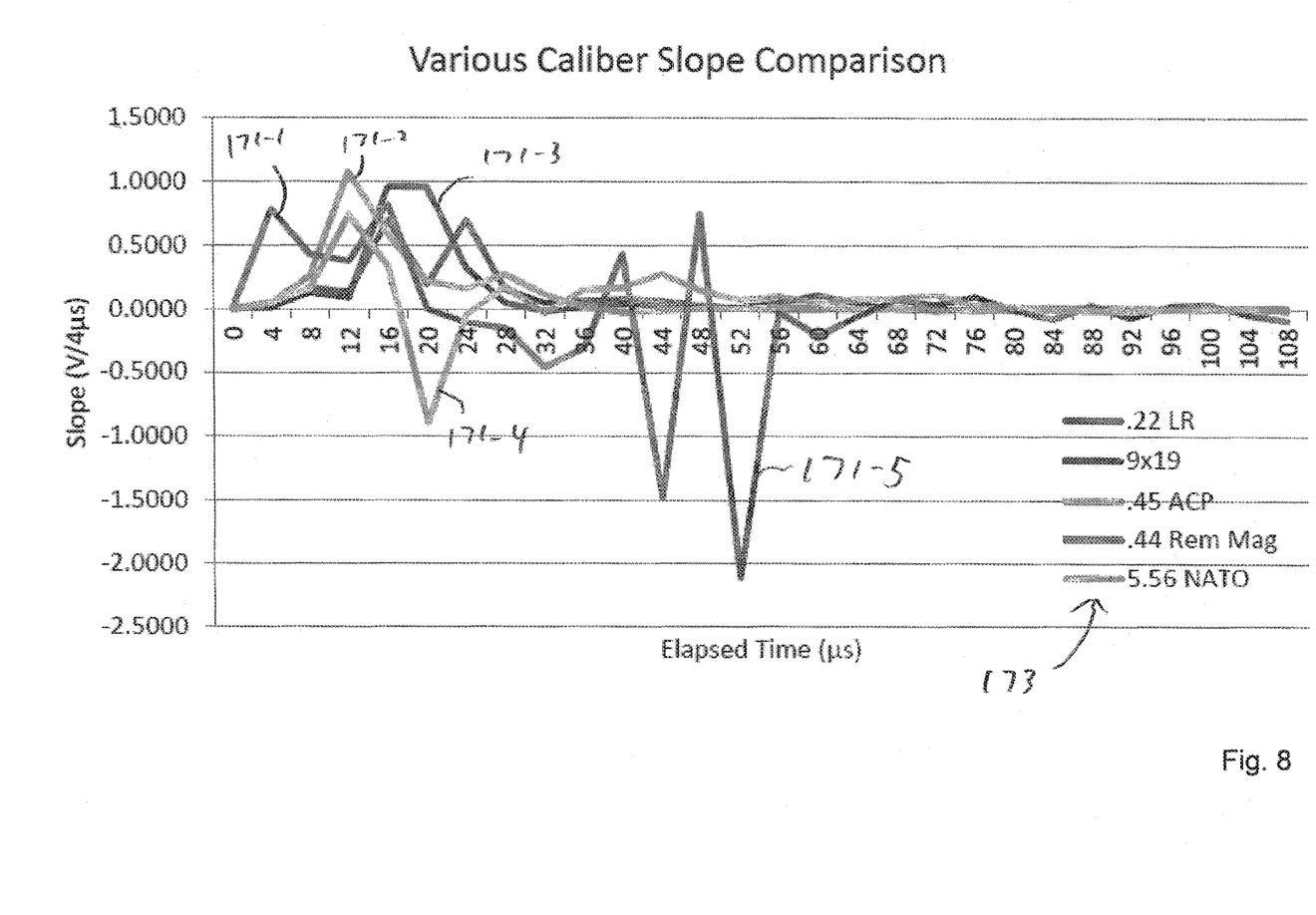
FIG. 8 shows graphs of sampled signatures for identifying projectile types in the graph of FIG. 5.

FIG. 8 shows graphs of sampled signatures for identifying projectile types in the graph of FIG. 5. Referring to FIGS. 1, 5, 7 and 8, the detection circuit 110 further comprises an interface to a ballistics database 118, in which the ballistics database stores a signature based on an impact slope 174 from previous projectile impacts for comparison and determination of a type of projectile from the computed impact slope. A plurality of graphs 171-1 ... 171-5 gathered from various impact incidents may be stored to depict characteristics such as the peak 172 and ancillary reverberation peaks 176, 178.

Configurations herein may also be employed in a monitoring and response system using network communications either directly from the detection circuit or in conjunction with a mobile device app on a device carried by the wearer. In such a system, in addition to transmitting an impact severity indicative of a projectile speed and force, and a location indicative of an injury site to a first responder dispatch, other parameters such as biometric or vital signs and the GPS location of the wearer may also be transmitted. Vital signs such as pulse, oxygen saturation (respiration), blood pressure, body temperature and other parameters that complement the impact intensity and location could also be determined and transmitted. Such addition information may further assist first responders in evaluating a condition of the wearer, as an impact in the upper chest/heart region combined with blood pressure or pulse gives a more accurate assessment of the exigency of the wearer. For example, an exigency score could be computed based on the impact location and severity, say the upper chest or heart region, and then adjusted based on whether the pulse is erratic or remains normal, indicating further detail about a distress level of the victim.

A further configuration applies to a tactical or multiple personnel deployment, as might be undertaken in response to a riot or battlefield context. A number of responders, each equipped for impact detection, GPS and biometric parameters, may be deployed into a hazardous area. Receipt of signals from multiple detection circuits 110 can assist in a triage of casualties to provide both the location and condition of wearers requiring immediate intervention, isolate those beyond help, and allow for later recovery of personnel with less severe injury. In the event that the wearer is in a continued hostile environment, selective deployment of recovery resources avoids placing first responders at unnecessary risk.

Those skilled in the art should readily appreciate that appropriate programs and methods defined herein are deliverable to a user processing and rendering device in many forms, including but not limited to a) information permanently stored on non-writeable storage media such as ROM devices, b) information alterably stored on writeable non-transitory storage media such as floppy disks, magnetic tapes, CDs, RAM devices, and other magnetic and optical media, or c) information conveyed to a computer through communication media, as in an electronic network such as the Internet or telephone modem lines. The operations and methods may be implemented in a software executable object or as a set of encoded instructions for execution by a processor responsive to the instructions. Alternatively, the operations and methods disclosed herein may be embodied in whole or in part using hardware components, such as Application Specific Integrated Circuits (ASICs), Field Programmable Gate Arrays (FPGAs), state machines, controllers or other hardware components or devices, or a combination of hardware, software, and firmware components.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. A projectile detection device for a protective garment, comprising:

an electrically resistive mesh in the protective garment and disposed between opposed planar sheets of a selectively conductive material, the opposed planar sheets configured for electrical communication in response to pressure exerted against the electrically resistive mesh;

a plurality of conductive members for applying a voltage to each of the opposed planar sheets; and a detection circuit for identifying an electrical communication between the opposed planar sheets, the detection circuit configured for determining, based on the identified electrical communication, a severity and location of a projectile impact causing a compressive force towards the opposed planar sheets, the detection circuit configured to:

sample a series of measurements indicative of the electrical communication and compute a change in the compressive force over time, such that a predetermined increase in the compressive force is indicative of the projectile impact; and compute an impact slope based on a sampling frequency and a decrease in resistance between samplings, the impact slope indicative of a ballistics type of a projectile causing the projectile impact.

2. The device of claim 1 wherein the conductive members further comprise a conductive sheet disposed on the selectively conductive material, the conductive members connected to the detection circuit.

3. The device of claim 2 wherein:
the conductive sheet further comprises a continuous conductive material having a low resistance sufficient to maintain a similar voltage across the conductive sheet;
the selectively conductive material has piezoelectric properties for exhibiting a variance in electrical characteristics in response to pressure; and
the mesh is an insulative material having a high resistance and adapted to permit electrical conduction or induction between the opposed planar sheets in response to compression.

4. The device of claim 1 wherein the opposed planar sheets further comprise orthogonal strips of the selectively conductive planar material adapted for electrical communication in response to a compressive force, the electrical communication defining a position of the compressive force based on corresponding locations on each of the opposed sheets of the selectively conductive material.

5. The device of claim 4 wherein the orthogonal strips define a grid having intersecting regions based on strips overlapping at a common position.

6. The device of claim 5 further comprising at least one electrode coupled between each strip and the detection circuit, the detection circuit configured to identify a location on the grid based on an intersection of strips having the lowest resistance.

7. The device of claim 6 wherein the conductive member, the opposed planar sheets and the mesh form a layered assembly responsive to a projectile impact such that electrical communication between the opposed planar sheets of the orthogonal strips on indicates a lowest resistance at a location of greatest compressive force from the projectile.

8. The device of claim 7 wherein the detection circuit is configured to sample each of the strips for an electrical communication with the conductive sheet on the opposed side and identify an impact when the electrical communication attains a threshold indicative of a projectile impact, the electrodes to the opposed strips having the lowest resistance indicative of the grid position at which the impact occurred, the grid corresponding to injury locations on a wearer of the protective garment.

9. The device of claim 1 wherein the opposed planar sheets further comprise a first series of elongated strips longitudinally adjacent and parallel to other strips of the first series, and orthogonal to a second series of strips.

10. The device of claim 1 wherein the detection circuit further comprises an interface to a ballistics database, the ballistics database storing a signature based on an impact slope from previous projectile impacts for comparison and determination of a type of projectile from the computed impact slope.

11. The device of claim 1 further comprising a communications interface attached to the detection circuit, the communications interface configured to transmit an impact severity indicative of a projectile speed and force, and a location indicative of an injury site to a first responder dispatch.

12. A method of detecting an impact and placement of a projectile, comprising:
disposing a plurality of selectively resistive elements on a wearable substrate adapted to cover a protected region, the selectively resistive elements responsive to pressure against the wearable substrate;
applying a voltage to the resistive elements for detecting a variation in an electrical resistance;
sampling the resistive elements for identifying a change in the electrical resistance; and
computing, based on a rate of the change, a severity of a projectile impact causing the identified change, and determining, based on the selectively resistive element experiencing the change, a location of the projectile impact, further comprising:
sampling a series of measurements indicative of the electrical resistance;
computing a change in the compressive force to the resistive elements over time by computing an impact slope based on a sampling frequency and a decrease in resistance between samplings, the impact slope indicative of a ballistics type of a projectile causing the projectile impact, wherein a predetermined increase in the compressive force is indicative of the projectile impact; and
comparing each of the sampled measurements to the predetermined increase for determining occurrence of a projectile impact.

13. The method of claim 12 further comprising determining, based on a point of maximum conduction between the opposed planer sheets, an impact location.

14. The method of claim 13 further comprising:
gathering and receiving biometric parameters from sensor elements disposed in conjunction with the wearable substrate;
transmitting the impact location, a GPS location, and the biometric parameters to a responsive entity, the responsive entity adapted to analyze the impact location and the biometric parameters for determining whether to deploy recovery resources to the GPS location.

15. The method of claim 14, further comprising:
receiving the impact location, GPS location and the biometric parameters from a plurality of deployed wearable substrates worn by field personnel; and
computing, for each wearable substrate, a triage score based on the impact location and biometric parameters; and
determining, based on the triage score, which of the GPS locations to deploy recovery resources to.

16. The method of claim 12 further comprising:
disposing the selectively resistive elements as opposed planar sheets, the opposed planar sheets further comprising a plurality of strips of the selectively conductive planar material adapted for electrical communication in response to a compressive force,
the electrical communication defining a position of the compressive force based on corresponding locations on the plurality of strips of the selectively conductive material.

17. The method of claim 16 further comprising disposing the strips in a series to run parallel to the strips on the same series and orthogonal to a second series of strips, the strips defining a grid having intersecting regions based on strips overlapping at a common position, further comprising:
connecting an electrode between each strip and the detection circuit; and
identifying a location on the grid based on an intersection of strips having the lowest resistance on each of the opposed sides of the mesh.

18. The method of claim 17 wherein sampling further comprises:
iterating through voltage readings sampled from resistive elements corresponding to both axes of the grid;

determining that an intersection of the strips of each axes having the lowest voltage is indicative of the grid location at which the impact occurred;

mapping the grid location to the protective garment for identifying an injury location; and transmitting an impact severity indicative of a projectile speed and force, and a location indicative of an injury site to a first responder dispatch.

19. A system for identifying a geographic location and severity of a projectile penetration, comprising:

a protective garment having an electrically resistive mesh disposed between opposed planar sheets of a selectively conductive material, the opposed planar sheets configured for electrical communication in response to pressure exerted against the electrically resistive mesh;

a plurality of conductive members for applying a voltage to each of the opposed planar sheets;

a detection circuit coupled to a mobile device app, the detection circuit configured to identify an electrical communication between the opposed planar sheets, the detection circuit configured for determining, based on the identified electrical communication, a severity and location of a projectile impact causing a compressive force towards the opposed planar sheets, the detection circuit configured to:

sample a series of measurements indicative of the electrical communication and compute a change in the compressive force over time, such that a predetermined increase in the compressive force is indicative of the projectile impact; and compute an impact slope based on a sampling frequency and a decrease in resistance between samplings, the impact slope indicative of a ballistics type of a projectile causing the projectile impact; and the mobile device app responsive to the detection circuit for transmitting an impact severity indicative of a projectile speed and force, and a location indicative of an injury site to a first responder dispatch.

\* \* \* \* \*